United States Patent
Sprotte et al.

(10) Patent No.: US 10,261,095 B2
(45) Date of Patent: Apr. 16, 2019

(54) PREDICTIVE BIOMARKERS OF CLINICAL RESPONSE TO ANTI-LPS IMMUNOGLOBULIN TREATMENT

(71) Applicants: JULIUS-MAXIMILIANS-UNIVERSITÄT WÜRZBURG, Würzburg (DE); IGNOVA GMBH, Lyons (FR)

(72) Inventors: Günter Sprotte, Rottenbuch (DE); Ana Maria Waaga-Gasser, Würzburg (DE)

(73) Assignees: JULIUS-MAXIMILIANS-UNIVERSITÄT WÜRZBURG, Würzburg (DE); IGNOVA GMBH, Oberursel (DE)

( * ) Notice: Subject to any disclaimer, the term of this patent is extended or adjusted under 35 U.S.C. 154(b) by 0 days.

(21) Appl. No.: 15/562,174

(22) PCT Filed: Apr. 14, 2016

(86) PCT No.: PCT/EP2016/058276
§ 371 (c)(1),
(2) Date: Sep. 27, 2017

(87) PCT Pub. No.: WO2016/166246
PCT Pub. Date: Oct. 20, 2016

(65) Prior Publication Data
US 2018/0080943 A1     Mar. 22, 2018

(30) Foreign Application Priority Data
Apr. 17, 2015   (EP) .................................... 15164087

(51) Int. Cl.
*A61K 39/00* (2006.01)
*C07K 16/12* (2006.01)
*G01N 33/68* (2006.01)
*C07K 16/44* (2006.01)
*G01N 33/569* (2006.01)
*G01N 33/92* (2006.01)
*C12Q 1/6883* (2018.01)
*C12Q 1/6876* (2018.01)

(52) U.S. Cl.
CPC ..... *G01N 33/6863* (2013.01); *C07K 16/1203* (2013.01); *C07K 16/44* (2013.01); *C12Q 1/6876* (2013.01); *C12Q 1/6883* (2013.01); *G01N 33/56911* (2013.01); *G01N 33/6866* (2013.01); *G01N 33/6869* (2013.01); *G01N 33/92* (2013.01); *A61K 2039/505* (2013.01); *C07K 2317/11* (2013.01); *C07K 2317/23* (2013.01); *C12Q 2600/106* (2013.01); *C12Q 2600/158* (2013.01); *G01N 2333/475* (2013.01); *G01N 2333/4756* (2013.01); *G01N 2333/521* (2013.01); *G01N 2333/54* (2013.01); *G01N 2333/5412* (2013.01); *G01N 2333/5421* (2013.01); *G01N 2333/5428* (2013.01); *G01N 2333/56* (2013.01); *G01N 2333/705* (2013.01);

*G01N 2333/70596* (2013.01); *G01N 2333/916* (2013.01); *G01N 2400/50* (2013.01); *G01N 2800/125* (2013.01); *G01N 2800/26* (2013.01); *G01N 2800/52* (2013.01)

(58) Field of Classification Search
None
See application file for complete search history.

(56) References Cited

U.S. PATENT DOCUMENTS

2014/0112937 A1   4/2014   Wesjohann et al.

OTHER PUBLICATIONS

Appelmelk, Ben et al., "Lactoferrin Is a Lipid A-Binding Protein," American Society for Microbilogy, Infection and Immunity, vol. 62, No. 6, 1994, pp. 2628-2632.
Flier, Jeffrey et al., "The Tumor Necrosis Factor Ligand and Receptor Families," The New England Journal of Medicine, vol. 334, No. 26, 1996, pp. 1717-1725.
Bellamy, Wayne et al., "Identification of the bactericidal domain of lactoferrin," Biochimica et Biophysica Acta, vol. 1121, 1992, pp. 130-136.
Bernard, Gordon et al., "The American-European Consensus Conference on ARDS," American Journal of Respiratory and Critical Care Medicine, vol. 149, 1994, pp. 818-824.
Buchman, Timothy et al., "Induction of heat shock response leads to apoptosis in endothelial cells previously exposed to endotoxin," The American Psychological Society, pp. 165-170.
Devitt, Andrew et al., "Human CD14 mediates recognition and phagocytosis of apoptotic cells," Letters to Nature, vol. 392, 1998, pp. 505-509.
Inubushi, Toshihiro et al., "Molecular Mechanisms of the Inhibitory Effects of Bovine Lactoferrin on Lipopolysaccharide-mediated Osteoclastogenesis," The Journal of Biological Chemistry, vol. 287, No. 28, pp. 23527-23536.
Louis, Konstantinos et al., "Bacterial translocation in an experimental model of multiple organ dysfunctions," Journal of Surgical Research, vol. 183, 2013, pp. 686-694.
Munshi, Neru et al., "Lipopolysaccharide-Induced Apoptosis of Endothelial Cells and Its Inhibition by Vascular Endothelial Growth Factor," The Journal of Immunology, vol. 168, 2002, pp. 5860-5866.
Pinzone, Marilia Rita et al., "Microbial Translocation in Chronic Liver Diseases," International Journal of Microbiology, 2012, pp. 1-12.

(Continued)

*Primary Examiner* — Brian Gangle
(74) *Attorney, Agent, or Firm* — Polsinelli PC

(57) ABSTRACT

The present invention relates to the biomarkers for predicting the clinical response to anti-LPS immunoglobulin treatments in patients in need thereof. In particular, the invention provides methods for predicting the clinical response to an anti-LPS immunoglobulin treatment in a patient in need thereof, said method comprising the steps of evaluating the expression of a predictive biomarker selected from the group consisting of CD14, CD68, TLR4, TLR7, IL6, IL8, IL10, IFN-alpha, IGF1, CXCL1, CXCL9, CXCL10, RAGE, GDNF, BCHE, and combination thereof, in said patient.

14 Claims, No Drawings

(56) References Cited

OTHER PUBLICATIONS

Polunovsky, Vitaly et al., "Induction of Endothelial Cell Apoptosis by TNF: Modulation by Inhibitors of Protein Synthesis," Experimental Cell Research, vol. 214, 1994, pp. 584-594.

Robaye, Bernard et al., "Tumor Necrosis Factor Induces Apoptosis (Programmed Cell Death) in Normal Endothelial Cells In Vitro," American Journal of Pathology, vol. 138, No. 2, 1991, pp. 447-453.

Takei, Yoshiyuki et al., "Apoptosis: A new mechanism of endothelial and Kupffer cell killing," Journal of Gastroenterology and Hepatology, vol. 10, 1995, pp. S65-S67.

Struff, W.G. et al., "Bovine colostrum as a biologic in clinical medicine: a review," International Journal of Clinical Pharmacology and Therapeutics, vol. 45, No. 1, 2007, pp. 193-202.

Katz, Russell, "Biomarkers and Surrogate Markers: An FDA Perspective," The Journal of the American Society for Experimental Neuro Therapeutics, vol. 1, 2004, pp. 189-195.

Struff, W.G. et al., "Bovine colostrum as a biologic in clinical medicine: A review—Part II," International Journal of Clinical Pharmacology and Therapeutics, vol. 46, No. 5, 2008, pp. 211-225.

Waaga-Gasser, A.M. et al., "Oral immunoglobulin induces mononuclear cell apoptosis in patients suffering from idiopathic chronic pain syndrome: Results from a pilot study," International Journal of Clinical Pharmacology and Therapeutics, vol. 47, No. 7, 2009, pp. 421-433.

Clark, Gary et al., "Prognostic factors versus predictive factors: Examples from a clinical trial of erlotinib," Molecular Oncology, vol. 1, 2008, pp. 406-412.

Oldenhuis, C.N.A.M. et al., "Prognostic versus predictive value of biomarkers in oncology," European Journal of Cancer, vol. 44, 2008, pp. 946-953.

Biswas, Priscilla et al., "Immunomodulatory effects of bovine colostrum in human peripheral blood mononuclear cells," New Microbiologica, vol. 30, 2007, pp. 447-454.

Mehta, Sunali et al., "Predictive and prognostic molecular markers for cancer medicine," Therapeutic Advances in Medical Oncology, vol. 2, No. 2, 2010, pp. 125-148.

International Search Report and Written Opinion dated Jun. 16, 2016 issued in corresponding International Application No. PCT/EP2016/058276.

PREDICTIVE BIOMARKERS OF CLINICAL RESPONSE TO ANTI-LPS IMMUNOGLOBULIN TREATMENT

RELATED APPLICATIONS

This application is a national stage application (under 35 U.S.C. § 371) of PCT/EP2016/058276, filed Apr. 14, 2016, which claims benefit of European application EP 15164087.7, filed Apr. 17, 2015, both of which are incorporated herein by reference in their entirety.

The present invention relates to the biomarkers for predicting the clinical response to anti-LPS immunoglobulin treatments in patients in need thereof. In particular, the invention provides methods for predicting the clinical response to an anti-LPS immunoglobulin treatment in a patient in need thereof, said method comprising the steps of evaluating the expression of a predictive biomarker selected from the group consisting of CD14, CD68, TLR4, TLR7, IL6, IL8, IL10, IFN-alpha, IGF1, CXCL1, CXCL9, CXCL10, RAGE, GDNF, BCHE, and combination thereof, in said patient.

BACKGROUND

There are growing evidence that a variety of chronic diseases are triggered, sustained or reinforced by systemic translocation of intestinal lipopolysaccharides (LPS) [Pinzone et al. 2012]. Bacterial lipopolysaccharide (LPS) is thought to be responsible for the multiple organ dysfunction syndrome [Louis et al. 2013] and the acute respiratory distress syndrome [Bernard et al., Am J Respir Crit Care Med 1994; 149: 818-824]. Both in vitro and in vivo studies have shown that administration of LPS causes a variety of reactions [Windsor et al. 1993; Louis et al. 2013]. In vitro studies indicate that LPS does not directly induce apoptosis of endothelial cells. Several investigations have pointed to LPS-induced tumor necrosis factor alpha (TNF-$\alpha$) as the cause of endothelial cell apoptosis [Bazzoni and Beutler N Engl J Med 1996; 334: 1717-1725; Buchman et al. Am J Physiol 1993, 265: H165-170; Polunovsky et al. Exp Cell Res 1994, 214: 584-594; Robaye et al. Am J Pathol 1991, 138: 447-453; Takei et al., J Gastroenterol Hepatol, 1995, 10: 65-67; Munshi et al. J Immunol. 2002 Jun. 1; 168(11): 5860-6].

LPS is also known to be attracted by CD14 on the surface of monocytic cells [Devitt et al. 1998; Tapping et al. Nature 1998; 392: 505-509]. Interestingly, it is widely believed that this reflects the first step in signal transduction via LPS.

Another question from the clinical perspective concerns the impact of a therapeutic intervention involving the LPS turnover on the overall apoptotic response. In this context, in the long-term, immunoglobulins may exert several beneficial immunological effects in patients affected with subclinical immune activation. This is primarily reflected by antibodies against bacterial LPS molecules and Lactoferrin which also exerts strong inhibitory LPS activity [Bellamy et al. Biochim Biophys Acta 1992; 1121: 130-136, Appelmelk et al Infection and Immunity 1994; 62(2): 2628-2632; Inubushi et al. 2012]. However, the whole spectrum of effects and specificities of the effector mechanisms of oral anti-LPS immunoglobulins has not been fully investigated. One key effector mechanism may be related to apoptosis in monocytic cells. The inventors have shown that a new therapeutic approach based on an oral administration of anti-LPS antibodies (immunoglobulins) lead to a significant or complete symptom relief in more than 50% of the patients in need of such treatment, e.g. with chronic pain syndromes (unpublished data).

The fit-for-purpose, scientific validation, and the overall clinical qualification of parameters for diseases triggered by LPS translocation and inflammation could dramatically change the current outlook on treatment of such diseases.

A predictive biomarker is associated with the likelihood of sensitivity or resistance (response) to a specific therapy (drug). The concept of a predictive biomarker is usually applied to individual patients with the goal of tailoring therapy to maximize efficacy. In more specific and practical terms, a predictive biomarker as herein demonstrated could assist the clinician in deciding which patients are responders to the anti-LPS immunoglobulin treatment.

Accordingly, one object of the present invention is to provide a reliable prognosis assay for determining individual patient clinical benefit of oral immunoglobulin therapy (i.e responder to oral anti-LPS immunoglobulin treatment) and for avoiding administering the anti-LPS immunoglobulin treatments to non-responders. Methods for selecting the responders prior to treating patients would allow for an individualized therapeutic decision, which in turn is of great psychological benefit for the patients, improves health outcomes and provides economic benefit for the community.

Another object of the present invention is to provide a prognosis assay which could be performed from a biological sample of the patient, preferably a blood sample.

A further object of the present invention is to provide a prognosis assay that would be highly specific, i.e. whereas at least 80%, or 90% or more preferably at least 95% and even more preferably at least 98% of the patients that are diagnosed as responder according the assay are indeed true responders to the LPS immunoglobulin treatments.

In order to fulfil this need, the inventors performed a laboratory screen focusing on a broad spectrum of immune parameters in patients before and after oral anti-LPS immunoglobulin treatment and comparing the results to those of healthy control individuals.

Thus, according to the method of the present invention, a selection of the patients can take place before these individuals receive the anti-LPS immunoglobulin treatment. This would relief mental stress to the patients and save costs. The results of the screen performed by the inventors demonstrated that 15 specific parameter profiles (i.e. the predictive biomarkers) enable to differentiate between responders and non-responders to a planned anti-LPS immunoglobulin treatment.

SUMMARY OF PREFERRED EMBODIMENTS

In one aspect, the invention relates to an in vitro method for predicting the response to an anti-LPS immunoglobulin treatment in a patient in need thereof, said method comprising the step of evaluating the expression of one or more biomarkers in a biological sample obtained from said patient, wherein said one or more biomarkers are selected from the group of predictive biomarkers consisting of CD14, CD68, TLR-4, TLR-7, IL-6, IL-8, IL-10, IFN-alpha, IGF-1, CXCL1, CXCL9, CXCL10, RAGE, GDNF and BCHE.

More specifically, said evaluating step comprises a step of quantifying expression of one or more of the selected predictive biomarkers in a biological sample of said patient to obtain expression values, and comparing each expression value to a corresponding control value, for example to corresponding expression values from healthy volunteers. In certain embodiments, such control value may be normalized mean expression value of corresponding biomarker that is observed in healthy subjects.

In a preferred embodiment, said anti-LPS immunoglobulin treatment is a composition for oral administration, for example, an IgY composition. In a specific embodiment, said IgY composition comprises IgY (or their antigen-binding portions), obtained from hens immunized with gram-negative bacteria or their LPS-containing portions, preferably obtained from at least two distinct bacterial species.

In another specific embodiment, that may be combined with the preceding embodiments, the method is applied for a human subject suffering from a chronic disease induced by activated monocytes (CD14+) in peripheral blood. Such chronic disease induced by activated monocytes (CD14+) in peripheral blood include, without limitation, idiopathic chronic pain syndromes including without limitation chronic widespread pain, fibromyalgia, and bladder syndrome;

migraine, chronic head and neck deceleration trauma, epicondylitis, impingement syndrome;

Graft vs host disease (GVHD), chronic inflammatory gastro intestinal diseases including without limitation Crohn's disease, ulcerative colitis, and irritable bowel syndrome;

crest syndrome, systemic lupus erythematodes, pemphigus vulgaris, sclerodoma; and, atherosclerosis.

In a specific embodiment of the method of the invention, the expression of 2, 3, 4, or 5 biomarkers among the 15 predictive biomarkers of the invention is evaluated.

In another specific embodiment that may be combined with the preceding embodiments, the biological sample is a blood sample.

In another specific embodiment that may be combined with the preceding embodiments, said expression is gene expression as quantified by real-time quantitative PCR.

In another specific embodiment, that may be combined with the preceding embodiments, said expression is protein biomarker expression as quantified by specific antibodies.

In another aspect, the invention relates to a method for treating a chronic disease induced by activated monocytes (CD14+) in peripheral blood, comprising administering a therapeutically efficient amount of an anti-LPS immunoglobulin composition to a patient affected with said chronic disease, wherein said patient is a responder to said anti-LPS immunoglobulin composition and wherein said responder has been selected by evaluating the expression of one or more predictive biomarkers selected from the group consisting of CD14, CD68, TLR-4, TLR-7, IL-6, IL-8, IL-10, IFN-alpha, IGF-1, CXCL1, CXCL9, CXCL10, RAGE, GDNF and BCHE. Typically, the method may comprises the steps of: (a) providing a biological sample from a patient; (b) quantifying the expression of one or more predictive biomarkers, as defined above, in said biological sample, and, (c) administering a therapeutically effective amount of said anti-LPS immunoglobulin composition to the patient only if said patient is predicted to be a responder to said anti-LPS immunoglobulin composition, based on the expression level of said one or more biomarkers.

DETAILED DESCRIPTION

Prognosis methods allowing prediction of a response to anti-LPS treatment in patients in need of such treatment are provided by the present invention. Particularly, it is provided herein methods and kits allowing prediction of a clinical response to anti-LPS treatment, such as an anti-LPS IgY treatment in patients suffering from chronic diseases induced by activated monocytes (CD14+) in peripheral blood.

According to the present invention, a set of 15 biomarkers that are, individually or in combination, predictive of high probability of clinical response to anti-LPS treatment has been identified. The identification of these predictive biomarkers was permitted due to the systematic quantification of a number of cytokines or cytokine receptors expressions in peripheral blood sample of responder vs non-responder patients.

Thus, a first object of the present invention consists of a method for predicting the response to an anti-LPS immunoglobulin treatment in a patient in need thereof, said method comprising the step of evaluating the expression of one or more biomarkers in a biological sample obtained from said patient, wherein said one or more biomarkers are selected from the group of predictive biomarkers consisting of CD14, CD68, TLR-4, TLR-7, IL-6, IL-8, IL-10, IFN-alpha, IGF-1, CXCL1, CXCL9, CXCL10, RAGE, GDNF and BCHE.

As it is shown in the examples herein, when comparing the expression level value of candidate biomarkers between responder and non-responder patients to anti-LPS treatment, the inventors have identified biomarkers with statistically different expression in responder subject when compared to either healthy subject and non-responder subjects, hereafter called the "predictive biomarkers" and listed in Table 1 below.

The Patient in Need of Anti-LPS Immunoglobulin treatment

The term "patient" and "subject" which are used herein interchangeably refer to any member of the animal kingdom, preferably a mammal, or a human being, including for example a subject that has or is suspected to have a chronic disease induced by activated monocytes (CD14+) in peripheral blood.

Anti-LPS immunoglobulin treatment have indeed been shown to be effective in patients suffering from chronic diseases induced by activated monocytes (CD14+) in peripheral blood. Said CD14+ monocytes are activated in the gastrointestinal tract by gram negative bacteria or parts thereof and lead to an overproduction of monocyte/macrophage-related cytokines.

Gram negative bacteria are part of the human gastrointestinal microbiome. In a physiologically healthy gastrointestinal environment, these gram-negative bacteria do not pose any risk to human health, as a certain degree of the endotoxin lipopolysaccharide LPS is tolerated by the human defense system. It is actually needed as a positive feedback to the host immune system.

In a pathologic situation, there can be an overgrowth of gram-negative bacteria and an increase in gastrointestinal mucosal permeability, triggered by mucositis. Both lead to an increased presence of lipopolysaccharide (LPS) and other components of gram negative bacteria such as flagella, surface proteins etc at the submucosal level and consequent increased contact with the innate immune system's pattern recognition receptors. Waaga-Gasser et al. 2009 [International Journal of Clinical Pharmacology and Therapeutics, Vol 47, No. 7/2009 (421-433)] have shown that patients showing idiopathic pain syndromes possess such activated monocytes which fail to go into apoptosis after they have been activated by LPS.

Therefore, LPS triggers activation of macrophages followed by a dysfunctional induction of apoptosis in these cells. The combination of the two leads to a positive feedback loop and a translocation of the LPS signal to systemic parts of the body, leading in essence to a subliminal chronic inflammation.

This chronic inflammation in turn leads to phenotype specific to symptomatic diseases.

Accordingly, in specific embodiments, those patients in need of such anti-LPS treatment suffer from one or more of the following chronic diseases, all being characterized by activated (CD14+) monocytes activated by LPS:

Diseases related with mechanisms of translocation:

Pain related diseases such as: idiopathic chronic pain syndromes (including without limitation chronic widespread pain, fibromyalgia, bladder syndrome migraine, head and neck deacceleration trauma, epicondylitis, impingement syndrome.

Diseases related with mechanisms of local LPS neutralization in the gut:

Graft vs host disease (GVHD), chronic inflammatory gastro intestinal diseases such as Crohn's disease, ulcerative colitis, irritable bowel syndrome, Autoimmune diseases such as:

crest syndrome, systemic lupus erythematodes, pemphigus vulgaris, sclerodoma,

Other diseases such as:

Atherosclerosis, osteoarthritis, dementia, Alzheimer's, and psychiatric diseases such as depression and schizophrenia.

In a specific embodiment, the method of the invention is applied to patients suffering from idiopathic pain syndrome, graft vs host disease (GVHD) and/or pemphigus vulgaris and epicondylitis, migraine, osteoarthritis, frozen shoulder or adhesive capsulitis, oral mucositis, carpal tunnel syndrome.

Anti-LPS Immunoglobulin Treatment

As used herein, an "anti-LPS immunoglobulin treatment" relates to any therapeutic treatment comprising, as the active principle, a substance or composition made of immunoglobulins or their antigen-binding portions, directed against lipopolysaccharide (LPS) or micro-organism producing such lipopolysaccharide or their LPS-containing portions.

As used herein, and as well understood in the art, "treatment" is an approach for obtaining beneficial or desired results, including clinical results. Beneficial or desired results can include but not limited to, alleviation or amelioration of one or more symptoms or conditions, diminishment of extent of disease, stabilized (i.e. not worsening) state of disease, preventing spread of disease, delay or slowing of disease progression, reversal of disease, amelioration or palliation of the disease state, and remission (whether partial or total).

Such anti-LPS immunoglobulin treatment has indeed been shown to be effective in treating patients suffering from chronic diseases induced by activated monocytes (CD14+) in peripheral blood as discussed above.

Preferred examples of such anti-LPS immunoglobulin treatment and their beneficial results in patients suffering from chronic disease induced by activated monocytes are described in WO2012136522 and WO2012136534.

In one specific embodiment, such anti-LPS immunoglobulin treatment comprises polyclonal antibodies or monoclonal antibodies raised against LPS-expressing microorganism or the LPS-containing portions, more preferably gram-negative bacteria or their LPS-containing portions.

As used herein the term "antibody" or "immunoglobulins" includes whole antibodies and any antigen binding fragments or derivatives (i.e., "antigen-binding portion") or single chains thereof. In specific embodiment, such antibody or immunoglobulin may include monoclonal or polyclonal antibodies or immunoglobulins, or immunoglobulins obtained from immunized animals or from recombinant cells, and their antigen-binding portions.

In naturally occurring antibodies, two heavy chains are linked to each other by disulfide bonds and each heavy chain is linked to a light chain by a disulfide bond. There are two types of light chain, lambda (l) and kappa (k). The light chain includes two domains, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, transplacental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from nonhypervariable or framework regions (FR) influence the overall domain structure and hence the combining site. Complementarity Determining Regions or CDRs refer to amino acid sequences which together define the binding affinity and specificity of the natural Fv region of a native immunoglobulin binding site. The light and heavy chains of an immunoglobulin each have each three CDRs, designated LCDR1, LCDR2, LCDR3 and HCDR1, HCDR2, HCDR3, respectively. An antigen-binding site, therefore, typically includes six CDRs, comprising the CDRs set from each of a heavy and a light chain V region. Framework Regions (FRs) refer to amino acid sequences interposed between CDRs. Each VH and VL is composed of three CDRs and four FRs arranged from amino-terminus to carboxy-terminus in the following order: FR1, CDR1, FR2, CDR2, FR3, CDR3, FR4.

Furthermore, although the two domains of the Fv fragment, VL and VH, are coded for by separate genes, they can be joined, using recombinant methods, by a synthetic linker that enables them to be made as a single chain protein in which the VL and VH regions pair to form monovalent molecules (known as single chain Fv (scFv); see e.g., Bird et al., 1988 Science 242:423-426; and Huston et al., 1988 Proc. Natl. Acad. Sci. 85:5879-5883). Such single chain antibodies are also intended to be encompassed within the term "antigen-binding portion" of an antibody. These antibody fragments are obtained using conventional techniques known to those of skill in the art, and the fragments are screened for utility in the same manner as are intact antibodies.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "recombinant antibody", as used herein, includes all antibodies that are prepared, expressed, created or isolated by recombinant means, such as antibodies isolated from an animal (e.g., a mouse) or a hybridoma prepared therefrom, antibodies isolated from a host cell transformed to express the antibody, e.g., from a transfectoma, antibodies isolated from a recombinant, combinatorial antibody library, and antibodies prepared, expressed, created or isolated by any other means that involve splicing of all or a portion of a immunoglobulin gene, sequences to other DNA sequences.

The term "immunoglobulin" also includes chimeric or humanized antibody.

The term "chimeric antibody" refers to an antibody which comprises a VH domain and a VL domain of a non-human antibody, and a CH domain and a CL domain of a human antibody.

According to the invention, the term "humanized antibody" refers to an antibody having variable region framework and constant regions from a human antibody but retains substantially the same CDRs of a non-human antibody.

In specific embodiments, the term "antigen-binding portions" refers to a fragment of an antibody or immunoglobulin which contains the variable domains comprising the CDRs of said antibody. The basic antibody fragments include Fab, Fab', F(ab')2 Fv, scFv, dsFv, and the like. For example of antibody fragment see also for review, Holliger et al Nature Biotechnology 23, issue 9 1126-1136 (2005).

The term "Fab" denotes an antibody fragment having a molecular weight of about 50,000 and antigen binding activity, in which about a half of the N-terminal side of H chain and the entire L chain, among fragments obtained by treating IgG with a protease, papaine, are bound together through a disulfide bond.

The term "F(ab')2" refers to an antibody fragment having a molecular weight of about 100,000 and antigen binding activity, which is slightly larger than the Fab bound via a disulfide bond of the hinge region, among fragments obtained by treating IgG with a protease, pepsin.

The term "Fab'" refers to an antibody fragment having a molecular weight of about 50,000 and antigen binding activity, which is obtained by cutting a disulfide bond of the hinge region of the F(ab')2.

A single chain Fv ("scFv") polypeptide is a covalently linked VH::VL heterodimer which is usually expressed from a gene fusion including VH and VL encoding genes linked by a peptide-encoding linker. "dsFv" is a VH::VL heterodimer stabilised by a disulfide bond. Divalent and multivalent antibody fragments can form either spontaneously by association of monovalent scFvs, or can be generated by coupling monovalent scFvs by a peptide linker, such as divalent sc(Fv)2.

Hens' naturally occurring immunoglobulins are like mammals' in having light (L) and heavy (H) chains, bridged by disulphide bonds. The molecule is made up of a variable part with an antigen binding site and a constant part. In the cases of hens a distinction is made between the immunoglobulins M (IgM), Y (IgY) and A (IgA). IgM has the same function as mammals' IgM. Present in all vertebrates, IgM delivers the first response with its high molecular weight. Results of recent genetic research suggest that the IgY molecule is phylogenetically a progenitor of mammals' IgG and IgE. Structurally there is a clear difference between IgY and mammals' IgG, as the heavy chain of hens' IgY has an additional constant domain instead of the hinge region of mammals' IgG. So the molecular weight of IgY is higher as compared to IgG. IgY, like mammals' IgG, is the immunoglobulin delivering the second response with its high serum-concentration and low molecular weight. In the literature, the terms IgG and IgY are sometimes used as synonyms as regards hens, so on the basis of the newest findings it has been decided within the framework of an international ECVAM workshop that the term IgY should be used throughout. (Schade et al 2005). As used herein however, the term IgY also includes any antigen-binding portions of such IgY.

"LPS-producing microorganisms" may typically be selected from gram-negative bacteria, most preferably selected from the group consisting of *Streptobacillus moniliformis*, meningococcus, *Chlamydophila, chlamydia*, spirochetes, *cyanobacteria*, species of the Proteobacteria phylum, in particular Enterobacteriaceae (*Escherichia coli, Salmonella, Shigella, Klebsiella, Proteus, Enterobacter*), Pseudomonas bacteria, Legionella bacteria, Neisseria bacteria, Rickettsia bacteria, Pasteurella multocida bacteria and species of the Bacteroidetes strain.

Said LPS-containing portions of LPS-producing microorganism may be any antigens capable of raising an immunological response against lipopolysaccharides produced by LPS-producing microorganism (also called LPS antigenic determinants).

In a specific embodiment, said anti-LPS immunoglobulin treatment comprises or essentially consists of immunoglobulin A, immunoglobulin D, immunoglobulin E, immunoglobulin M, immunoglobulin G and/or immunoglobulin Y, or their antigen-binding portions.

In a specific embodiment, said anti-LPS immunoglobulin treatment comprises bovine IgG, more specifically colostrum-derived bovine IgG, or their antigen-binding portions.

In a preferred embodiment, said anti-LPS immunoglobulin treatment comprises anti-LPS IgY composition, most preferably, polyclonal IgY antibodies raised against gram-negative bacteria, or their antigen-binding portions.

In a preferred embodiment which may be combined with the previous embodiment, IgY polyclonal antibodies have been obtained at least partially from egg yolk powder, preferably from defatted or partially defatted egg yolk powder.

Defatted or partially defatted egg yolk powder is obtained by standard processes (removal of fat from liquid egg yolk or dried egg yolk powder), preferably by using ultrafiltration, water dilution, filtration, gel electrophoresis, chromatography, hexane or supercritical $CO_2$. After the removal of fat, the defatted liquid egg yolk or egg yolk powder is dried via lyophilization or spray drying.

The IgY composition obtained from egg yolk typically comprise, for example, lipoproteins, such as HDL and LDL, and the water-soluble proteins of the egg yolk, α-livetin (80 kDa), β-livetin (45 kDa) and/or γ-livetin (150 kDa), which also comprise most of the enzymes found in the egg (Ternes, Acker and Scholtyssek, Ei and Eiprodukte, 1994).

In order to obtain anti-LPS IgY from hens (or their eggs), hens may advantageously be immunized by LPS-producing microorganisms.

In a specific embodiment, said anti-LPS immunoglobulin treatment comprises anti-LPS IgY composition, or their antigen-binding portions, obtained from egg yolk of hens immunized with gram-negative bacteria or their LPS-containing portions, preferably from at least two distinct gram-negative bacterial species.

For example, said IgY composition suitable for the preparation of an anti-LPS treatment may be obtained by the following method:

a) immunizing at least 2 distinct groups of hens, each group with LPS-producing gram-negative bacteria, wherein each group is given a different bacterial species, b) obtaining the antibody-containing fraction from each of the at least 2 distinct groups, c) mixing the at least 2 antibody-containing fractions so that the resulting antibody preparation comprises at least 3% of each antibody fraction directed against each bacterial species or their LPS-containing portions thereof by weight of the total antibody content, and, preferably, the total amount of each specific antibodies against each microorganism species is >=7% by weight of the total antibody content.

According to the above specific production method, an anti-LPS immunoglobulin treatment may be an IgY composition which comprises at least 2 specific antibody fractions which target distinct lipopolysaccharide-expressing gram-negative bacteria, for example between 2 and 10 specific antibody fractions; each specific antibody fraction in each case have an antibody content of at least 3% by weight of the total antibody content of the antibody preparation; and, preferably, the total amount of such specific antibody fractions against lipopolysaccharide-expressing microorganisms is >=7% by weight of the total antibody content of the antibody preparation.

In specific embodiments, said IgY composition comprising antibody fractions directed against gram-negative bacteria selected from the group consisting of *E. coli, Salmonella, Shigella, Klebsiella, Proteus* and *Enterobacter*. More specifically, in one preferred embodiment, said IgY composition comprises one fraction consisting of polyclonal IgY directed against *Escherichia coli* and another fraction consisting of polyclonal IgY directed against *Salmonella typhimurium*.

More preferably, each specific antibody fraction account for at least 4% by weight based on the total antibody content of the IgY composition, and even more preferably, the total amount of said specific antibodies is >=10% by weight respectively based on the total antibody content of the antibody preparation.

In one specific embodiment, said anti-LPS treatment is formulated for oral administration.

Preferably, said anti-LPS treatment is an IgY composition as described above for oral administration.

The Prognosis Method

The methods of the invention enable to predict the response of a patient to an anti-LPS immunoglobulin treatment.

As used herein, the term "predict" refers to a method that allows determining with a high level of probability (statistically significant), prior to treatment, if a patient will respond to said treatment. Accordingly, the term "predict" does not necessarily consist of an absolute response. Rather, it may consist of a response allowing to determine a higher probability of the patient to be a good responder, as compared to the average probability in a population.

As used herein, a "response to anti-LPS immunoglobulin treatment" or equally a "clinical response to anti-LPS immunoglobulin treatment" is observed when at least one of the symptoms of a disease to be treated by said anti-LPS immunoglobulin is decreased after treatment as compared to said symptom prior to the treatment. In specific embodiments, said symptom of the chronic disease is pain, for example specific pain symptom associated to the chronic disease as measured by a daily summed up score (NRS) by said patient (NRS-pain score values). In such specific embodiment, a response to anti-LPS immunoglobulin treatment is a significant decrease of the mean value of NRS-pain score values after treatment (for example during a 5-day period) as compared to the mean value of corresponding NRS-pain score values prior to treatment.

As used herein, the term "decrease" or "increase" means a statistically significant decrease or increase of a control value, preferably, at least 10%, at least 20%, at least 30%, at least 40%, at least 50%, at least 90%, or at least 99% decrease or increase of the control value. According to the methods of the invention, the patient is predicted to be responder or non-responder based on evaluation of the expression of one or more of the predictive biomarkers in a biological sample, prior to the treatment.

The term "responder" as used herein means a patient that demonstrates or is likely to demonstrate a positive treatment response to anti-LPS immunoglobulin treatment. In an embodiment, a responder is a patient suffering from idiopathic pain syndromes who demonstrates or is likely to demonstrate significant pain relief or even total relief of at least one pain symptom after treatment.

The term "non-responder" as used herein means a patient that does not demonstrate or is not likely to demonstrate a positive treatment or a response to anti-LPS immunoglobulin treatment.

In an embodiment, a non-responder is a patient suffering from idiopathic pain syndromes and that does not demonstrate or is not likely to demonstrate any significant pain relief of any of the pain symptoms after treatment.

The methods of the invention thus comprises the step of (a) quantifying the expression of one or more predictive biomarkers in a biological sample obtained from said patient and (b) comparing the obtained expression values to corresponding control values.

As used herein, the term "biological sample" is intended to include tissues, cells, biological fluids and isolates thereof, isolated from a subject, as well as tissues, cells and fluids present within a subject, provided that said biological sample is susceptible to contain (i) peripheral blood cells or (ii) nucleic acids or proteins that are produced by the peripheral blood cells from the patient.

In a specific embodiment, said biological sample for use in the methods of the invention is a blood sample, including, peripheral blood cell sample and proteins.

Quantifying the Expression of a Predictive Biomarker

The prediction method of the invention comprises a step of evaluating the expression of one or more of the predictive biomarkers in a biological sample.

As used herein, the term "evaluating" typically include the steps of (a) quantifying the expression of one or more of the selected predictive biomarkers in a biological sample obtained from said subject to obtain expression values, and (b) comparing the obtained each expression value of said predictive biomarkers to corresponding control values, wherein differences in the expression values compared to the respective control values is indicative that the subject is a responder to anti-LPS immunoglobulin treatment.

Expression of the biomarkers can be quantified by determining gene or protein expression of the predictive biomarkers in the biological sample of a subject, for example a blood sample. The quantification may be relative (by comparing the amount of a biomarker to a control with known amount of biomarker for example and detecting "higher" or "lower" amount compared to that control) or more precise, at least to determine the specific amount relative to a known control amount.

The terms "nucleic acid" and "polynucleotide" are used interchangeably and refer to a polymeric form of nucleotides of any length, either deoxyribonucleotides or ribonucleotides or analogs thereof. Polynucleotides can have any three-dimensional structure and may perform any function. The following are non-limiting examples of polynucleotides: a gene or gene fragment, exons, messenger RNA (mRNA), cDNA, isolated DNA of any sequence, isolated RNA of any sequence, nucleic acid probes, and primers. A polynucleotide can comprise modified nucleotides, such as methylated nucleotides and nucleotide analogs. If present, modifications to the nucleotide structure can be imparted before or after assembly of the polymer. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form. A "gene" refers to a polynucleotide containing at least one open reading frame (ORF) that is capable of encoding a particular polypeptide or protein after being transcribed and translated. A polynucleotide sequence can be used to identify larger fragments or full-length coding sequences of the gene with which they are associated. Methods of isolating larger fragment sequences are known to those of skill in the art. "Gene expression", "gene product" or "expression" are all used herein interchangeably and refer to the nucleic acids or amino acids (e.g., peptide or polypeptide) generated when a gene is transcribed and translated, cDNA or RNA sequence of the biomarker; biomarker gene expression, biomarker protein expression, biomarker mRNA expression; functional effect of the biomarker protein, functional effect of the biomarker gene, cDNA or mRNA, protein, cDNA, gene or mRNA activity.

In a particular embodiment "gene expression", "gene product" or "expression" denotes mRNA expression, cDNA expression, protein transcription and protein expression.

The term "polypeptide" is used interchangeably with the term "protein" and in its broadest sense refers to a compound of two or more subunit amino acids. The subunits can be linked by peptide bonds.

Such quantification methods may alternatively include detection and quantification of the corresponding gene expression level of said predictive biomarker which encompasses the quantification of corresponding mRNA of said predictive biomarker, for example by performing Real-Time quantitative PCR, as well as by using DNA microarrays, i.e. substrate onto which are bound nucleic acids, at defined position, that specifically hybridize with the cDNA corresponding to amplified mRNA of said predictive biomarker.

Typically, in specific embodiments, a mixture of transcribed polynucleotides (mRNA) obtained from the biological sample of the patient is subjected to reverse transcription and quantitative amplification. Said cDNA or mRNA may be detected by in vitro techniques either by stringent hybridization to DNA microarrays or Northern blots.

In any cases, a general principle of such detection and quantification assays involve preparing a sample or reaction mixture that may contain a predictive biomarker and a probe under appropriate conditions and for a time sufficient to allow the predictive biomarker and probe to interact and bind, thus forming a complex that can be detected (and quantified) in the reaction mixture.

These detection and/or quantification assays of a biomarker can be conducted in a variety of ways. Appropriate conditions to the particular assay and components thereof will be well known to one skilled in the art.

In a particular embodiment, the level of predictive biomarker mRNA can be determined both by in vitro formats in a biological sample using methods known in the art.

Specific methods for quantifying a biological marker for the purpose of carrying out the prediction methods of the invention are described hereunder. Those methods include Luminex and ELISA quantification methods as described in the Examples.

Quantifying Predictive Biomarkers by cDNA Microarrays

According to this embodiment, a microarray may be constructed based on one or a combination of 2, 3, 4, 5 or 6 of the 15 predictive biomarkers that are disclosed throughout the present specification. Probes for these biomarkers may be placed on the microarray. These probes may be different than those used in PCR methods. However, they should be designed and used in conditions such that only nucleic acids (mRNA or cDNA or PCR amplificates of cDNA material) having the predictive biomarkers may hybridize and give a positive result.

In a preferred embodiment, the array will further include one or more control probes. In specific embodiments, said probes may be oligonucleotides that range from about 5 to about 500 or about 5 to about 200 nucleotides, more preferably from about 10 to about 100 nucleotides and most preferably from about 15 to about 70 nucleotides in length. In other particularly preferred embodiments, the probes are about 20 or 25 nucleotides in length. In another preferred embodiment, test probes are double or single strand DNA sequences. DNA sequences may be isolated or cloned from natural sources or amplified from natural sources using natural nucleic acid as templates. These probes have sequences complementary to particular subsequences of the genes of the predictive biomarkers whose expression they are designed to detect.

In addition to test probes that bind the target nucleic acid(s) of interest (corresponding gene expression of one or more of the predictive biomarkers), the microarray can contain a number of control probes. The control probes may fall into three categories referred to herein as normalization controls; expression level controls; and mismatch controls. Normalization controls are oligonucleotide or other nucleic acid probes that are complementary to labeled reference oligonucleotides or other nucleic acid sequences that are added to the nucleic acid sample. The signals obtained from the normalization controls after hybridization provide a control for variations in hybridization conditions, label intensity, "reading" efficiency and other factors that may cause the signal of a perfect hybridization to vary between arrays. In a preferred embodiment, signals (e.g. fluorescence intensity) read from all other probes in the array are divided by the signal (, fluorescence intensity) from the control probes thereby normalizing the measurements. Virtually any probe may serve as a normalization control. However, it is recognized that hybridization efficiency varies with base composition and probe length. Preferred normalization probes are selected to reflect the average length of the other probes present in the array; however, they can be selected to cover a range of lengths. The normalization control(s) can also be selected to reflect the (average) base composition of the other probes in the array, however in a preferred embodiment, only one or a few probes are used and they are selected such that they hybridize well (i.e., no secondary structure) and do not match any target-specific probes.

Expression level controls are probes that hybridize specifically with constitutively expressed genes in the biological sample. Virtually any constitutively expressed gene provides a suitable target for expression level controls.

Typical expression level control probes have sequences complementary to subsequences of constitutively expressed "housekeeping genes" including the beta-actin gene, the RNA18S, the transferrin receptor gene, the GAPDH gene, Ubiquitin C (UBC) gene, ribosomal protein large P0 (RPLPO) gene, beta-2-microglobulin (B2M), hypoxanthine phosporibosyltransferase 1 (HPRT1) gene, TATA box binding protein (TBP) gene, peptidylprolyl isomerase A (PPIA) gene, glucuronidase beta (GUSB) gene, and phosphoglycerate kinase 1 (PGK1) gene.

Solid supports containing oligonucleotide probes for differentially expressed genes can be any solid or semisolid support material known to those skilled in the art. Suitable examples include, but are not limited to, membranes, filters, tissue culture dishes, polyvinyl chloride dishes, beads, test strips, silicon or glass based chips and the like. Suitable glass wafers and hybridization methods are widely available. Any solid surface to which oligonucleotides can be bound, either directly or indirectly, either covalently or non-covalently, can be used. In some embodiments, it may be desirable to attach some oligonucleotides covalently and others non-covalently to the same solid support. A preferred solid support is a high density array or DNA chip. These contain a particular oligonucleotide probe in a predetermined location on the array. Each predetermined location may contain more than one molecule of the probe, but each molecule within the predetermined location has an identical sequence. Such predetermined locations are termed features.

Quantifying Predictive Biomarkers by Real-Time Quantitative PCR

Methods to quantify nucleic acids (for example mRNAs of the predictive biomarkers) may include real time quantitative PCR methods (RT-qPCR). RT-qPCR is based on the detection of a fluorescent report molecule that increases as PCR product accumulates with each cycle of amplification. Fluorescent reporter molecules include dyes that bind double-stranded DNA (e.g. SYBR Green I) or sequence-specific probes (e.g. Molecular Beacons or TaqMan® Probes). Such methods include multiplex quantitative methods which allow to quantify in parallel expression of a plurality of predictive biomarkers.

For example, for quantifying the predictive biomarkers of the invention by use of RT-qPCR methods, a blood cell sample of a patient is collected. Said blood cells are lysed and total RNA is extracted according to standard methods.

Total RNA extract is then subjected to reverse transcription followed by real-time quantitative PCR (for example, as described in the examples).

Detecting and Quantifying Biomarker Polypeptides

Expression level of the biomarker can also be determined by examining protein expression or the protein product of at least one of the predictive biomarkers. Determining the protein level involves measuring the amount of any immunospecific binding that occurs between an antibody that selectively recognizes and binds to the polypeptide of the biomarker in a sample obtained from a patient and comparing this to the amount of immunospecific binding of at least one biomarker in a control sample. The amount of protein expression of the biomarker can be increased or reduced when compared with control expression. Alternatively, a combination of more than one of the predictive biomarkers can be assayed.

Various methods are known in the art for detecting protein expression levels in such biological samples, including various immunoassays methods. They include but are not limited to radioimmunoassays, ELISA (enzyme linked immunosorbent assays), "sandwich" immunoassays, immunoradiometric assays, in situ immunoassays (using e.g., colloidal gold, enzyme or radioisotope labels), western blot analysis, immunoprecipitation assays, immunofluorescent assays, flow cytometry, immunohistochemistry, confocal microscopy, enzymatic assays, surface plasmon resonance and PAGE-SDS.

Determining the protein level involves for example measuring the amount of any immunospecific binding that occurs between an antibody that selectively recognizes and binds to the polypeptide of the biomarker in a sample obtained from a patient. These assays may also include direct binding of labelled antibody to a target biomarker.

Sandwich assays are among the most useful and commonly used assays. A number of variations of the sandwich assay technique exist, and all are intended to be encompassed by the present invention. Briefly, in a typical forward assay, an unlabeled antibody is immobilized on a solid substrate, and the sample to be tested brought into contact with the bound molecule. After a suitable period of incubation, for a period of time sufficient to allow formation of an antibody-antigen complex, a second antibody specific to the antigen, but labeled with a reporter molecule capable of producing a detectable signal is then added and incubated, allowing time sufficient for the formation of another complex of antibody-antigen-labeled antibody. Any unreacted material is washed away, and the presence of the antigen is determined by observation of a signal produced by the reporter molecule. The results may either be qualitative, by simple observation of the visible signal, or may be quantitated by comparing with a control sample containing known amounts of biomarker.

Variations on the forward assay include a simultaneous assay, in which both sample and labeled antibody are added simultaneously to the bound antibody. These techniques are well known to those skilled in the art, including any minor variations as will be readily apparent. In a typical forward sandwich assay, a first antibody having specificity for the biomarker is either covalently or passively bound to a solid surface.

The binding processes are well-known in the art and generally consist of cross-linking covalently binding or physically adsorbing, the polymer-antibody complex is washed in preparation for the test sample. An aliquot of the sample to be tested is then added to the solid phase complex and incubated for a period of time sufficient (e.g. 2-40 minutes or overnight if more convenient) and under suitable conditions (e.g. from room temperature to 40° C. such as between 25° C. and 32° C. inclusive) to allow binding of any subunit present in the antibody. Following the incubation period, the antibody subunit solid phase is washed and dried and incubated with a second antibody specific for a portion of the biomarker. The second antibody is linked to a reporter molecule which is used to indicate the binding of the second antibody to the molecular marker.

An alternative method involves immobilizing the predictive biomarkers in the sample and then exposing the immobilized biomarkers to specific antibody which may or may not be labeled with a reporter molecule. Depending on the amount of biomarker target and the strength of the reporter molecule signal, a bound biomarker target may be detectable by direct labelling with the antibody. Alternatively, a second labeled antibody, specific to the first antibody is exposed to the target-first antibody complex to form a target-first antibody-second antibody tertiary complex. The complex is detected by the signal emitted by the reporter molecule.

By "reporter molecule", as used in the present specification, is meant a molecule which, by its chemical nature, provides an analytically identifiable signal which allows the detection of antigen-bound antibody. The most commonly used reporter molecules in this type of assay are either enzymes, fluorophores or radionuclide containing molecules (i.e. radioisotopes) and chemiluminescent molecules.

In the case of an enzyme immunoassay or ELISA assay, an enzyme may typically be conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, -galactosidase and alkaline phosphatase, amongst others. The substrates to be used with the specific enzymes are generally chosen for the production, upon hydrolysis by the corresponding enzyme, of a detectable colour change. Examples of suitable enzymes include alkaline phosphatase and peroxidase. It is also possible to employ fluorogenic substrates, which yield a fluorescent product rather than the chromogenic substrates noted above. In all cases, the enzyme-labeled antibody is added to the first antibody-molecular marker complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of biomarker which was present in the sample.

Alternatively, fluorescent compounds, such as fluorescein and rhodamine, may be chemically coupled to antibodies without altering their binding capacity. When activated by illumination with light of a particular wavelength, the fluorochrome-labeled antibody adsorbs the light energy, inducing a state to excitability in the molecule, followed by emission of the light at a characteristic color visually detectable with a light microscope. As in the EIA, the fluorescent labeled antibody is allowed to bind to the first antibody-molecular marker complex. After washing off the unbound reagent, the remaining tertiary complex is then exposed to the light of the appropriate wavelength, the fluorescence observed indicates the presence of the molecular marker of interest. Immunofluorescence and EIA techniques are both very well established in the art. However, other reporter molecules, such as radioisotope, chemiluminescent or bioluminescent molecules, may also be employed.

Comparing Expression Level of Predictive Biomarkers to a Control Value

In specific embodiment of the prediction method of the invention, the quantifying step thus allows to obtain an "expression value" for each biomarker tested in the biological sample, for use in the comparing step.

For ease of use in the comparing step, said expression value may consist of a normalized (relative) value which is obtained after comparison of the absolute expression level value with a reference value, said reference value consisting for example of the expression level value of reference proteins in the biological sample.

Each expression level value obtained after quantification of the expression of one or more of the predictive biomarkers in a patient prior to treatment, is compared with a corresponding control value, allowing to determine whether the patient is a responder or a non-responder.

Preferably, said expression level value consists of a normalized relative value which is obtained after comparison of the absolute expression level value with a normal value, said normal value consisting of the expression level value of constitutive (or reference) genes, such as housekeeping genes β-actin, 18S RNA or peptidylprolyl isomerase A (PPIA).

Said control value may be for example, the mean value of normalized (relative) mean value of healthy subjects, responder patients and/or non-responder patients. Examples of such normalized mean value are given in the examples below for each of the 15 predictive biomarkers.

Said control value can also be determined by routine experimentation depending on the quantification methods and the predictive biomarkers that will be used for the methods of the invention.

For example, said control value corresponds to the expression level value observed for non-responder patients, and a patient is predicted to be a responder when the expression level value is statistically different from the control value, for example increased as compared to a control value, or decreased as compared to a control value.

Alternatively, said control value corresponds to the expression level value observed for responder patients, and a patient is predicted to be a responder when the expression level value is statistically not different from the control value.

The comparison referred to in step (b) of the methods of the invention may be carried out manually or computer assisted.

For a computer-assisted comparison, the expression values may be compared to control values which are stored in a database by a computer program. The computer program may further evaluate the result of the comparison, i.e. automatically provide the desired assessment in a suitable output format.

As it is shown in the examples, each of the predictive biomarkers according to the invention listed herein is relevant for predicting a response to an anti-LPS immunoglobulin treatment, since all the biomarkers have a P value equal or inferior to 0.0001 except for IL6 and BCHE predictive biomarker.

Statistical relevance may be improved by combining the predictive biomarkers in the assays. In specific embodiments, the expression level of 2 predictive biomarkers, or 3, 4, 5, 6, 7 or even 8, out of the 15 predictive biomarkers of the invention, is evaluated.

Any combination of two, three, four or more of predictive biomarkers is encompassed by the methods of the invention: Specific combinations of predictive biomarkers for use in the methods of the invention are listed hereafter:

(i) CD14+TLR4+IGF-1+IL-8+IFN-alpha+CXCL10+GDNF (ii) CD14+TLR4+IGF-1+IL-8+IFN-alpha+RAGE (iii) CD14+CD68+TLR4+IGF-1+IL-8+IFN-alpha (iv) CD14+TLR4+IGF-1+IL-8+IFN-alpha (v) CD14+TLR4+IGF-1+IL-8

(vi) CD14+TLR4+IGF-1+IFN-alpha (vii) CD14+TLR4+IGF-1+RAGE or other combinations with the mentioned markers.

The comparing step may not necessarily include a separate comparison of the expression values of each biomarker with their corresponding control values. In specific embodiments, a multi-biomarker score value can be obtained by combining together the expression values or their normalized values and compared to a corresponding multibiomarker score control value.

The Predictive Biomarkers

The 15 predictive biomarkers of the invention of the present invention are described hereafter by their acronym names, also termed herein "gene symbols", according to Genbank nomenclature:

TABLE 1

List of predictive biomarkers

| Biomarker | UniprotKB/Swiss-Prot[1] |
|---|---|
| CD14 | P08571 |
| CD68 | P34810 |
| TLR4 | O00206 |
| TLR7 | Q9NYK1 |
| IL6 | P05231 |
| IL8 | P10145 |
| IL10 | P22301 |
| IFNα | P01562 |
| IGF1 | P05019 |
| CXCL1 | P09341 |
| CXCL9 | Q07325 |
| CXCL10 | P02778 |
| RAGE (=AGER) | Q15109 |
| GDNF | P39905 |
| BCHE | P06276 |

[1]http://www.uniprot.org/

In the present invention, when referring to the biomarkers, as already explained above, it may alternatively refer either to the gene (polynucleotide) encoding said biomarker, any of its expression product, including transcript RNA molecules or corresponding cDNAs or the protein and/or its post-translational modifications.

As shown in the Table 2 in the examples, the relative expression value dCt of the predictive biomarkers CD14, C68, TLR4, TLR7, IL2, IL6, IL8, IFNα, CXCL1, CXCL9, CXCL10, GDNF, RAGE and IGF1 has been shown to be significantly lower in responder patients as compared to the corresponding relative expression value in non-responder patients.

The relative expression value of the predictive biomarker BCHE has been shown to be significantly higher in responder patients as compared to the corresponding relative expression value in non-responder patients.

Assaying for Biomarker Expression and the Treatment with Anti-LPS Immunoglobulin Once a patient has been predicted to be a responder to anti-LPS immunoglobulin treatment, administration of a suitable anti-LPS immunoglobulin treatment only to said responder patient can be effected in one dose, continuously or intermittently throughout the course of treatment.

Methods of determining the most effective means and dosage of administration are well known to those of skill in the art and will vary with the composition used for therapy, the purpose of the therapy, and the subject being treated. Single or multiple administrations can be carried out with the dose level and pattern being selected by the treating physician. Suitable dosage formulations and methods of administering the agents may be empirically adjusted. Preferably, oral formulations are used.

If a patient is predicted to be a non-responder to anti-LPS immunoglobulin treatment, alternative therapies may be preferred.

At least one of the biomarkers selected from Table 1 can be assayed, prior to administration of anti-LPS treatment. Alternatively, more than one, for example 2, 3, 4, 5, 6, 7, or 8, or all of the 15 biomarkers selected from Table 1 can be assayed together.

Kits of the Invention

The invention also relates to a kit for carrying out the prediction methods of the invention as disclosed above. The kit may comprise a plurality of reagents, each of which is capable of binding specifically with one or more of the predictive biomarkers (either its nucleic acid or protein). Suitable reagents for such kit include antibodies or nucleic acids. For example, such kits include a DNA microarray as described above. Such kit may alternatively comprise, primers and probes for carrying out RT-qPCR on one or more of the predictive biomarkers as listed in Table 1.

The monitoring or prediction kit of the invention may thus include a plurality of reagents, each of which is capable of binding specifically with a gene or protein specific of one of the predictive biomarkers. Suitable reagents for binding specifically with a protein biomarker include, without limitation, antibodies.

In specific embodiments, the kit comprises specific reagents for quantifying the following group of biomarkers:
 (i) CD14+TLR4+IGF-1+IL-8+IFN-alpha+CXCL10+ GDNF;
 (ii) CD14+TLR4+IGF-1+IL-8+IFN-alpha+RAGE;
 (iii) CD14+CD68+TLR4+IGF-1+IL-8+IFN-alpha;
 (iv) CD14+TLR4+IGF-1+IL-8+IFN-alpha;
 (v) CD14+TLR4+IGF-1+IL-8;
 (vi) CD14+TLR4+IGF-1+IFN-alpha; or,
 (vii) CD14+TLR4+IGF-1+RAGE,
or other combinations with the above mentioned specific biomarkers.

EXAMPLES

Preparation of Anti-LPS IgY Treatment

The manufacturing process of the drug substance for the below samples comprised four main steps. The first step was the IgY egg production via vaccination of six herds of hens (Gallus gallus domesticus) with antigen preparations of inactivated whole cell bacteria of *Escherichia coli* F18 and *Salmonella typhimurium, Porphyromonas gingivalis, Clostridium perfringens C, Streptococcus mutans*, and the fungal cells of *Candida albicans* respectively. Six distinct hen herds were held. Each herd was immunized with one of the above mentioned antigens. The second step was the egg processing including egg yolk separation, pasteurization and egg yolk spray drying. The third step was the delipidation with hexane and the stabilization with oligosaccharides, which was followed by the fourth step, the preparation of the drug substance by mixing equal amounts of the delipidated egg yolk powders from the six vaccinated herds. The mixed delipidated egg yolk powder (drug substance) was not further formulated. It was given to the patients and swallowed with water. Alternatively it could be mixed into plain yoghurt and then eaten. Specific IgY activity was measured by competitive ELISA using respective in house standards.

Example 1: Predictive Biomarkers in Patients Suffering from Idiopathic Chronic Pain Syndrome Studied Patient Cohort Patients (n=40) were included if they had chronic idiopathic pain irrespective of classification and no acceptable response to any symptomatic treatment (chronic intractable pain syndromes). Those with allergy against egg components were excluded. The patients were treated over a period of 4 weeks. The dosage during the first 2 weeks of IgY treatment was 1.25 g twice daily followed by 2.5 g twice daily during the last two weeks. The therapeutic effects were assessed via both clinical and laboratory parameters. Thereby, the laboratory parameters underwent a blinded assessment. The protocol used was approved by the local medical ethics committee and informed consent was given by the patient prior to sample acquisition.

Clinical Parameters

Patient pain diaries containing a daily summed up score (numeric rating scale NRS) of pain and 5 quality of life parameters. The pain diary had the option of daily documentation of three differently classified pain symptoms (patients suffering from long standing idiopathic pain present in the majority of cases more than one chronic pain syndrome). Patients with more than one chronic pain entity graded them in their personal perception of pain intensity, once before the start of the trial (pain 1=highest grade, pain 3=lowest grade).

The primary clinical end point of the study was defined as the change of the two mean NRS-pain score values of at least one of the three pain symptoms.

Primary Endpoint

The change in pain diary VAS-pain score between the mean value of the 5-day period prior to the start and the 5-day period prior to the end of the study. A reduction of at least 2 points on the numeric rating scale (NRS) of at least one of the three constant pain syndromes was defined as a positive result. Efficacy of the delipidated egg yolk powder containing the target IgY could be shown. The respective patients were named "Responders".

Secondary Endpoints (i) Change in "quality of life parameters" (pain diary data) between the mean value of the 5-day period prior to the start and the 5-day period prior to the end of the study. A reduction of at least 2 points on the numeric rating scale (NRS) was defined as a positive result.

(ii) Significant changes of biomarker values between the pre and end of treatment values (represent responder patients).

(iii) Significant laboratory differences between the mean pre-therapeutic laboratory values of responders vs. non-responders (for the identification of response-predictive biomarker).

(iv) Incidence and severity of unexpected adverse reactions

From a total of 40 patients, peripheral blood from 38 individuals was analyzed and compared with peripheral blood of untreated healthy volunteers (n=30).

Real Time PCR

The qRT-PCR was carried out as followed: Peripheral blood was taken from the patients with chronic diseases (chronic pain syndromes) treated with IgY at the University of Wurzburg, Germany, at two time points: (i) Before the beginning of the treatment with IgY (T1=week 0) and (ii) after four weeks of treatment with IgY (T2=week 4).

For this purpose 40 ml EDTA peripheral blood was taken from the patients at both time points. To obtain the blood cells, one part of EDTA-blood plus five parts Lysis Buffer (Fa. Qiagen) was mixed and kept for 15 min at room temperature (RT). Then the tubes were centrifuged by 311 g for 10 Min and the supernatant discarded. The pellet of peripheral blood mononuclear cells (PBMCs) was washed with RPMI 1640 Medium (Fa.Gibco). This procedure was performed three times. The cells were counted and $5 \times 10^6$ cells/ml were diluted using "freeze medium", (i.e. inactivated fetal calf serum (FCS, Fa. Gibco)+10% Dimethylsulfoxid (DMSO, Fa. Sigma) and stored at −80° C.).

Gene expression was analyzed using reverse transcription following quantitative real-time PCR (RT-qPCR). Reverse transcription from total RNA to cDNA was carried out by using High Capacity cDNA Reverse Transcription Kit (Life Technologies, Carlsbad, Calif.) according to the manufacturer's instructions.

Gene quantification was performed using (i) Taqman Gene Expression Master Mix (Life Technologies) and Taqman Gene Expression Assays (Life Technologies) according to the manufacturer's instructions. Analysis was performed on a Biorad CFX96 Touch Real-Time PCR Detection System (Biorad, Hercules, Calif.). Quantification data were analyzed with the Biorad CFX Manager Analysis software (Biorad) and Microsoft Excel 2010 (Microsoft Corporation, Redmond, Wash.) and (ii) MESA GREEN qPCR MasterMix Plus for SYBR® Assay (Eurogentec, Seraing, Belgium) and RT2 qPCR Primer Assays (Qiagen, Hilden, Germany). For preparation of the reaction mix 12.5 µl MESA GREEN qPCR MasterMix Plus for SYBR® Assay, 9.5 µl dH2O and 1.0 µl RT2 qPCR Primer Assay were mixed and 2.0 µl cDNA dilution (containing 100 ng cDNA) was added.

Analysis was performed on a Biorad CFX96 Touch Real-Time PCR Detection System (Biorad, Hercules, Calif.) according to the manufacturer's instructions. Quantification data were analyzed with the Biorad CFX Manager Analysis software (Biorad) and Microsoft Excel 2010 (Microsoft Corporation, Redmond, Wash.).

Housekeeping genes β-actin, 18S RNA and PPIA were used for relative quantification. Reproducibility was confirmed by duplicates of each sample. The average threshold cycle (Ct) value was calculated as the cycle number at which the fluorescence of the reporter reaches a fixed threshold. The difference (dCt) between the average Ct values of the samples in the target wells and those of the housekeeping genes was assessed.

Identification of Predictive Biomarkers of Therapeutic Response

Blood samples were taken before study start (prior to first dose of DYP IgY product intake) and at the last day of the study.

The following biomarkers were analyzed: Interleukin (IL)-1α, IL-1β, IL-1Rα, IL-2, IL-2R, IL-4, IL-5, IL-6, IL-7, IL-8, IL-10, IL-12, IL-13, IL-15, IL-17, IL-18, Interferon (IFN)-α, IFN-γ, Tumornekrosefaktor (TNF)-α, TNF-RI, TNF-RII, chemokine (C-C motif) ligand 2 (CCL2), CCL3, CCL4, CCL5, CCL7, CCL8, CCL11, Chemokine receptor (CXCR) 3, chemokine (C-X-C motif) ligand 1 (CXCL1), CXCL9, CXCL10, CXCL12, CXCL13, Granulocyte-macrophage colony-stimulating factor (GM-CSF), Insulin-like growth factor 1 (IGF-1), nuclear factor kappa-light-chain-enhancer of activated B cells (NF-κB), Cyclooxygenase (COX)-2, Receptor for Advanced Glycation Endproducts (RAGE), High-mobility group protein B1 (HMGB1), heat shock protein (HSP)70, HSP90, CD14, CD19, CD20, CD21, CD45, CD68, toll like receptor (TLR)2, TLR3, TLR4, TLR7, TLR8, TLR9, Substance P, Leukotriene B4 (LTB4), Fractalkin, Epidermal growth factor (EGF), Vascular endothelial growth factor (VEGF), Basic fibroblast growth factor (FGF basic), glial cell line-derived neurotrophic factor (GDNF), Butyrylthiocholine (BChE).

Protein and gene expression levels were determined. Protein levels of IL-1α, IL-1β, IL-1Rα, IL-2, IL-2R, IL-4, IL-5, IL-6, IL-7, IL-8, IL-10, IL-12, IL-13, IL-15, IL-17, IL-18, IFN-α, IFN-β, TNF-α, TNF-RI, TNF-RII, CCL2, CCL3, CCL4, CCL5, CCL7, CCL8, CCL11, CXCR3, CXCL1, CXCL9, CXCL10, CXCL12, CXCL13, GM-CSF, EGF, VEGF, and FGF basic were measured in duplicate in the serum samples using immunobead-based multiplex assays (Luminex analysis), Panels of capture antibody-coated beads and labeled detection antibodies were purchased from Biosource, (Camarillo, Germany). The reagents were pre-tested and qualified by the manufacturer to ensure the absence of cross-reactivity among antibody-coated beads. The assays were performed using the Bio-Plex System (Biosource). Immunoassays (ELISA) were used according the manufacturer's instructions to measure human IGF-1, Substance P, LTB4, RAGE, and BChE in patient serum (R&D Systems, Wiesbaden, Germany).

To determine the amount of the cells flow cytometry (FACS) analysis were used at each of the two time points were analyzed in peripheral blood samples obtained from the patients and separated on Lymphoprep® according to the manufacturer's instructions (Nycomed Pharma, Oslo, Norway). Cells ($5\times10^5$) were stained with PE-conjugated anti-CD14, anti-CD68, FITC-conjugated anti-CD45 and 7 AAD, PE-conjugated anti-CD25, FITC-conjugated anti-CD3 and 7 AAD and PE-conjugated anti-mouse IgG2a. All antibodies were purchased from Beckman Coulter (Krefeld, Germany). Four-color flow cytometry was performed on a FACS-Epics XL-MCL (Beckman Coulter) and cells were analyzed using Expo 32 acquisition software (Beckman Coulter). Viable lymphocytes were gated and $10^5$ events were collected.

Results 38 patients completed the study, 24 women and 14 men; their mean age was 54 years and the mean duration of pain history 12.6 years.

All 38 patients documented the course of at least one pain, 30 patients documented the course of at least two and 26, the course of three differently classified pain syndromes.

Analysis of variance (ANOVA) showed significant pain relief for the responder study patient group to the IgY treatment, and in addition, pain relief was significant for pain syndrome 1, 2 and 3 when responders were grouped together. That means that as a group the responders patients on average showed significant relief in one pain syndrome as well as the same relief in their second and third pain entity.

24 out of 38 subjects completing the study were identified as IgY responders in accordance to the definition of the primary endpoint.

All 24 IgY responders fulfilled both the clinical and laboratory response criteria.

14 Subjects were identified as IgY non-responders missing both clinical and laboratory response criteria Relevant laboratory parameters (gene expression) could be identified as potentially predictive biomarkers for therapeutically relevant IgY efficacy.

The two patients dropped out of the study due to violation of the protocol and one from persistent cough, which happened some days before the end of the study.

The major therapeutic effects resulted during the second part of the study under an IgY dosage of $2\times2.5$ g.

Statistical analysis and identification of predictive biomarkers chosen as a potentially predictive marker for the IgY-treatment.

Each used parameter was compared between healthy volunteers and non-responders or responders as well as non-responders and responders using a T-test. Furthermore, each of the parameters was also compared between healthy volunteers together with non-responders and responders using an one way ANOVA. The statistical programme used was the GraphPad Prism5. The parameters which were significantly different, $p<0.05$ between healthy volunteers and non-responders and responders were chosen as a potentially predictive marker for the IgY-treatment.

The table 2 below shows the relative expression data for each predictive biomarker between responder and non-responder groups with P values showing statistical significance:

TABLE 2

Comparison of expression values of predictive biomarkers in responder, and non-responder

| Predictive biomarker | Relative expression (dCt) in Responder group | Relative expression (dCt) in Non-responder group | P value |
|---|---|---|---|
| CD14 | 5.627 ± 0.2718 N = 21 | 9.959 ± 0.3561 N = 11 | <0.0001 |
| CD68 | 4.718 ± 0.1754 N = 21 | 8.449 ± 0.2215 N = 11 | <0.0001 |
| TLR4 | 10.58 ± 0.2286 N = 21 | 13.48 ± 0.2675 N = 10 | <0.0001 |
| TLR7 | 9.885 ± 0.1858 N = 21 | 11.87 ± 0.2018 N = 10 | <0.0001 |
| IL2 | 13.10 ± 0.5763 N = 10 | 16.82 ± 0.1823 N = 7 | 0.0001 |
| IL6 | 11.72 ± 0.6477 N = 16 | 15.96 ± 0.2643 N = 8 | 0.0002 |
| IL8 | 6.323 ± 0.3445 N = 21 | 8.775 ± 0.3917 N = 11 | 0.0001 |
| IFNα | 12.80 ± 0.4354 N = 13 | 15.38 ± 0.3370 N = 12 | 0.0001 |
| CXCL1 | 8.510 ± 0.3240 N = 21 | 11.43 ± 0.2247 N = 10 | <0.0001 |
| CXCL9 | 11.45 ± 0.2191 N = 16 | 14.37 ± 0.1162 N = 9 | <0.0001 |
| CXCL10 | 11.94 ± 0.2639 N = 20 | 14.20 ± 0.2041 N = 9 | <0.0001 |
| GDNF | 6.403 ± 0.2769 N = 20 | 9.058 ± 0.3319 N = 11 | <0.0001 |
| RAGE | 5.935 ± 0.2236 N = 21 | 10.59 ± 0.5092 N = 10 | <0.0001 |
| BCHE | 12.38 ± 0.3535 N = 5 | 9.952 ± 0.6549 N = 9 | 0.0227 |
| IGF1 | 11.68 ± 0.2025 N = 21 | 13.83 ± 0.1611 N = 11 | <0.0001 |

Conclusions

The polyvalent anti gram-negative whole bacteria Immunoglobulin Y offers a completely new approach to treat idiopathic pain syndromes even in patients with very late stages of chronification and highlights the first time a new common pathogenic mechanism as one major component in a very complex aetiology of a broad spectrum of phenotypes of chronic pain.

The oral application of polyvalent anti-gram negative whole bacteria Immunoglobulin Y resulted in a sustainable pain relief in more than 60% of patients (therapeutic responders).

Predictive biomarkers were identified, distinguishing not only between healthy subjects and pain patients but also between patients responding to IgY treatment and those not responding. This observation offers the availability of a prognostic laboratory screening test for pre-application oral polyvalent anti-gram negative whole bacteria Immunoglobulin Y therapy response testing.

Through this observation a representative example of potential predictive markers allowing to identify the patient population with such markers in their blood as a treatment response criteria for the anti-LPS immunoglobulin therapy.

REFERENCES

Pinzone M R, Celesia B M, Di Rosa M, Cacopardo B, Nunnari G. Microbial translocation in chronic liver diseases. Int J Microbiol 2012; 2012:694629. doi: 10.1155/2012/694629.

Louis K, Netea M G, Carrer D P, Kotsaki A, Mylona V, Pistiki A, Savva A, Roditis K, Alexis A, Van der Meer J W, Giamarellos-Bourboulis E J. Bacterial translocation in an experimental model of multiple organ dysfunctions. J Surg Res 2013; 183(2):686-694. doi: 10.1016/j.jss.2013.01.064.

Munshi N1, Fernandis A Z, Cherla R P, Park I W, Ganju R K. Lipopolysaccharide-induced apoptosis of endothelial cells and its inhibition by vascular endothelial growth factor. J Immunol. 2002; 168(11):5860-5866.

Tapping R I, Orr S L, Lawson E M, Soldau K, Tobias P S. Membrane-anchored forms of lipopolysaccharide (LPS)-binding protein do not mediate cellular responses to LPS independently of CD14. J Immunol. 1999; 162(9):5483-5489.

Inubushi T, Kawazoe A, Miyauchi M, Kudo Y, Ao M, Ishikado A, Makino T, Takata T. Molecular Mechanisms of the Inhibitory Effects of Bovine Lactoferrin on Lipopolysaccharide-mediated Osteoclastogenesis. J Biol Chem. 2012; 287(28):23527-23536. doi: 10.1074/jbc.M111.324673.

Schade R, Calzado E G, Sarmiento R et al. Chicken egg yolk antibodies (IgY-technology): a review of progress in production and use in research and human and veterinary medicine. Altern Lab Anim. 2005; 33(2):129-154

The invention claimed is:

1. A method for treating chronic disease induced by CD14+ activated monocytes in peripheral blood, comprising administering a therapeutically efficient amount of an anti-LPS immunoglobulin composition to a patient affected with said chronic disease, wherein said patient is a responder to said anti-LPS immunoglobulin drug and wherein said responder has been selected by evaluating the expression level of one or more biomarkers selected from the group consisting of CD14, CD68, Toll-like Receptor (TLR)-4, TLR-7, Interleukin (IL)-6, IL-8, IL-10, Interferon (IFN)-alpha, Insulin-like Growth Factor 1 (IGF-1), chemokine CXC motif ligand 1 (CXCL1), chemokine CXC motif ligand 9 (CXCL9), chemokine CXC motif ligand 10 (CXCL10), Receptor for Advanced Glycation Endproducts (RAGE), Glial cell line-Derived Neurotrophic Factor (GDNF) and Butyrylthiocholine (BCHE) in the patient, and identifying a decrease in the expression level of TLR-4, TLR-7, IL-6, IL-8, IL-10, IFN-alpha, IGF-1, CXCL1, CXCL9, CXCL10, RAGE, and/or GDNF compared to a control expression level and/or by identifying an increase in the expression level of BCHE relative to a control expression level.

2. The method of claim 1, wherein the evaluating step includes (a) quantifying the expression of one or more of the selected biomarkers in a biological sample obtained from said patient to obtain an expression value for each quantified biomarker, and (b) comparing each expression value obtained at step (a) to a corresponding control value.

3. The method of claim 2, wherein said control value corresponds to expression value observed in non-responder patients, responder patients and/or healthy subjects.

4. The method of claim 1, wherein the expression of 2, 3, 4, or 5 biomarkers among the selected biomarkers is quantified.

5. The method of claim 1, wherein said anti-LPS immunoglobulin treatment is a therapeutically efficient amount of an IgY composition.

6. The method of claim 1, wherein said chronic disease induced by CD14+activated monocytes in peripheral blood is selected from the group consisting of:
idiopathic chronic pain syndromes,
migraine, chronic head and neck deceleration trauma, epicondylitis, impingement syndrome,
Graft vs host disease (GVHD), chronic inflammatory gastro intestinal diseases,
crest syndrome, systemic lupus erythematosus, pemphigus vulgaris, scleroderma, and,
osteoarthritis and atherosclerosis.

7. The method of claim 5, wherein said IgY composition is administered orally to the patient.

8. The method of claim 5, wherein said IgY composition is obtained from hens immunized with gram-negative bacteria or of their LPS-containing portions.

9. The method of claim 5, wherein said IgY composition is obtained from hens immunized with at least two distinct species of gram-negative bacteria or of their LPS-containing portions.

10. The method of claim 6, wherein said idiopathic chronic pain syndrome is selected from the group consisting of chronic widespread pain, fibromyalgia, frozen shoulder or adhesive capsulitis, oral mucositis, carpal tunnel syndrome, and bladder syndrome.

11. The method of claim 6, wherein said chronic inflammatory gastrointestinal disease is selected from the group consisting of Crohn's disease, ulcerative colitis, and irritable bowel syndrome.

12. The method of claim 1, wherein said patient is identified as a responder to said anti-LPS immunoglobulin drug by quantifying the expression level of one or more of said biomarkers in a biological sample obtained from said patient to obtain an expression value for each quantified biomarker and comparing each obtained expression value to an expression value observed in non-responder patients, wherein a decrease of at least 10% in the obtained expression value of TLR-4, TLR-7, IL-6, IL-8, IL-10, IFN-alpha, IGF-1, CXCL1, CXCL9, CXCL10, RAGE, and/or GDNF relative to the expression value observed in non-responder patients and/or an increase of at least 10% in the obtained expression value of BCHE relative to the expression value observed in non-responder patients identifies said patient as a responder to said anti-LPS immunoglobulin drug.

13. The method of claim 1, wherein the expression level of at least three of said biomarkers is evaluated in the patient.

14. The method of claim 1, wherein the expression level of at five of said biomarkers is evaluated in the patient.

* * * * *